(12) United States Patent
Lee et al.

(10) Patent No.: US 10,525,264 B2
(45) Date of Patent: Jan. 7, 2020

(54) STIMULATOR AND METHOD OF CONTROLLING STIMULATOR

(71) Applicant: SAMSUNG ELECTRONICS CO., LTD., Suwon-si (KR)

(72) Inventors: Hyungwoo Lee, Seoul (KR); JongPal Kim, Seoul (KR); Seungchul Jung, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 48 days.

(21) Appl. No.: 15/789,552

(22) Filed: Oct. 20, 2017

(65) Prior Publication Data

US 2018/0133471 A1 May 17, 2018

(30) Foreign Application Priority Data

Nov. 16, 2016 (KR) .................. 10-2016-0152419
Aug. 7, 2017 (KR) .................. 10-2017-0099744

(51) Int. Cl.
*A61N 1/36* (2006.01)
*A61N 1/32* (2006.01)

(52) U.S. Cl.
CPC ............. *A61N 1/36* (2013.01); *A61N 1/328* (2013.01); *A61N 1/36003* (2013.01)

(58) Field of Classification Search
CPC .......... A61N 1/02; A61N 1/04; A61N 1/0456; A61N 1/05; A61N 1/0529; A61N 1/0551; A61N 1/32; A61N 1/36; A61N 1/378
See application file for complete search history.

(56) References Cited

U.S. PATENT DOCUMENTS

| | | | |
|---|---|---|---|
| 4,917,093 | A | 4/1990 | Dufresne et al. |
| 5,447,525 | A | 9/1995 | Powell et al. |
| 7,783,339 | B2 | 8/2010 | Lee et al. |
| 8,788,056 | B2 | 7/2014 | King et al. |
| 8,994,409 | B2 | 3/2015 | Yao et al. |
| 9,014,813 | B2 | 4/2015 | Foutz et al. |
| 9,061,152 | B2 | 6/2015 | Shi et al. |

(Continued)

FOREIGN PATENT DOCUMENTS

| | | |
|---|---|---|
| EP | 1 121 177 A1 | 8/2001 |
| EP | 1 575 664 A1 | 9/2005 |

(Continued)

OTHER PUBLICATIONS

Partial European Search Report dated May 9, 2018 in corresponding European Application No. 17201116.5 (16 pages in English).

(Continued)

*Primary Examiner* — George Manuel
(74) *Attorney, Agent, or Firm* — NSIP Law

(57) ABSTRACT

A stimulator and a method of controlling the stimulator are provided. The method includes determining a waveform of a stimulus signal for a target, based on biological feedback of the target responding to a first stimulus signal, calculating a bioimpedance of the target based on a voltage waveform measured by applying the stimulus signal with the determined waveform to the target, and determining an operating voltage of the stimulator based on the determined waveform and the calculated bioimpedance.

29 Claims, 8 Drawing Sheets

(56) References Cited

U.S. PATENT DOCUMENTS

| | | |
|---|---|---|
| 9,174,051 B2 | 11/2015 | Marnfeldt et al. |
| 9,393,430 B2 | 7/2016 | Demers et al. |
| 2013/0338732 A1 | 12/2013 | Foutz et al. |
| 2015/0328451 A1 | 11/2015 | Kobayashi |
| 2016/0067497 A1* | 3/2016 | Levine ................ A61B 5/6877 607/62 |
| 2016/0184592 A1 | 6/2016 | Marnfeldt et al. |

FOREIGN PATENT DOCUMENTS

| | | |
|---|---|---|
| JP | 2010-75401 A | 4/2010 |
| JP | 2012-210375 A | 11/2012 |
| JP | 2015-47363 A | 3/2015 |
| JP | 5963412 B2 | 7/2016 |
| WO | WO 2011/005607 A1 | 1/2011 |

OTHER PUBLICATIONS

Pallás-Areny, Ramón et al.,"Bioelectric Impedance Measurements Using Synchronous Sampling", *IEEE Transactions on Biomedical Engineering*, vol. 40, Issue 8, Aug. 1993 (pp. 1-6).

Lanmüller, H., et al. "Implantable device for long-term electrical stimulation of denervated muscles in rabbits," *Medical and Biological Engineering and Computing*, vol. 43, Issue 4, Aug. 2005, (pp. 535-540).

Uranga, Arantxa et al., "Electrode—Tissue Impedance Measurement CMOS ASIC for Functional Electrical Stimulation Neuroprostheses", *IEEE Transactions on Instrumentation and Measurement*, vol. 56, Issue 5, Oct. 2007 (pp. 2043-2050).

Extended European Search Report dated Nov. 8, 2019 in counterpart European Application No. 17201116.5 (18 pages in English).

\* cited by examiner

STIMULATOR AND METHOD OF CONTROLLING STIMULATOR

CROSS-REFERENCE TO RELATED APPLICATION(S)

This application claims the benefit under 35 USC § 119(a) of Korean Patent Application No. 10-2016-0152419, filed on Nov. 16, 2016, and Korean Patent Application No. 10-2017-0099744, filed on Aug. 7, 2017, in the Korean Intellectual Property Office, the entire disclosures of which are incorporated herein by reference for all purposes.

BACKGROUND

1. Field

The following description relates to a stimulator and a method of controlling the stimulator.

2. Description of Related Art

A stimulator applies an electrical stimulation to a body part, for example, a brain, a heart or a muscle. Based on a reaction of the body part to the electrical stimulation, treatment, rehabilitation or cosmetics may be performed. In an example, the stimulator applies an electrical stimulation with an appropriate strength to a paralyzed muscle, to recover a function of the paralyzed muscle. The stimulator applies a current of a preset waveform to a body part based on an operating voltage. Characteristics, for example, impedances, may vary depending on body parts. When an operating voltage of the stimulator is determined regardless of characteristics for each body part, a power efficiency of the stimulator is reduced.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, there is provided a method of controlling a stimulator, the method including determining a waveform of a stimulus signal for a target, based on biological feedback of the target responding to a first stimulus signal, calculating a bioimpedance of the target based on a voltage waveform measured by applying the stimulus signal with the determined waveform to the target, determining an operating voltage of the stimulator based on the determined waveform and the calculated bioimpedance, and controlling the stimulator to stimulate the target based on the determined waveform and the determined operating voltage.

The determining of the waveform may include determining the waveform by adjusting a stimulus strength and a stimulus duration of the first stimulus signal.

The determining of the waveform may include determining an optimum stimulus strength to minimize a power consumption of the stimulator, based on a first biological feedback to a stimulus signal of a maximum stimulus duration and a gradually increasing stimulus strength, determining an optimum stimulus duration to minimize the power consumption of the stimulator, based on a second biological feedback to a stimulus signal of the optimum stimulus strength and a gradually increasing stimulus duration, and determining the waveform based on the optimum stimulus strength and the optimum stimulus duration.

The determining of the optimum stimulus strength may include sensing initial biological feedback to the stimulus signal that may be based on the maximum stimulus duration and the gradually increasing stimulus strength, determining a stimulus strength corresponding to the sensed initial biological feedback as a rheobase current, and determining the optimum stimulus strength to be twice the rheobase current.

The determining of the optimum stimulus duration may include sensing initial biological feedback to the stimulus signal that may be based on the optimum stimulus strength and the gradually increasing stimulus duration, determining a stimulus duration corresponding to the sensed initial biological feedback as a chronaxie time, and determining the optimum stimulus duration as the chronaxie time.

The bioimpedance may include a resistance and a capacitance of the target.

The calculating of the bioimpedance may include detecting a voltage of a first point and a voltage of a second point from the voltage waveform, and calculating a resistance and a capacitance of the target based on the voltage of the first point and the voltage of the second point.

The calculating of the bioimpedance may include calculating a resistance of the target based on a first voltage measured in response to charges being injected by the stimulus signal with the determined waveform, and calculating a capacitance of the target based on a second voltage measured in response to charges being extracted by the stimulus signal with the determined waveform.

The resistance may be calculated using the equation $$R_E = \frac{V_1 - V_{DD}/2}{I_{STIM}}$$

wherein $R_E$ denotes the resistance, $V_1$ denotes the first voltage, $V_{DD}$ denotes an initial operating voltage of the stimulator, and $I_{STIM}$ denotes a stimulus strength based on the determined waveform.

The capacitance may be calculated using the equation $$C_E = \frac{I_{STIM} \times T_{STIM}}{V_2 - V_{DD}/2 + I_{STIM} \times R_E}$$

wherein $C_E$ denotes the capacitance, $I_{STIM}$ denotes a stimulus strength based on the determined waveform, $T_{STIM}$ denotes a stimulus duration based on the determined waveform, $V_2$ denotes the second voltage, $V_{DD}$ denotes an initial operating voltage of the stimulator, and $R_E$ denotes the resistance.

The determining of the operating voltage may include calculating a compliance voltage of the stimulator based on the determined waveform and the bioimpedance, and determining the operating voltage to be greater than the compliance voltage.

The compliance voltage may be calculated using the equation $V_C = 2 \times (I_{STIM} \times R_E + I_{STIM} \times T_{STIM}/C_E + V_{OV})$ wherein $V_C$ denotes the compliance voltage, $I_{STIM}$ denotes a stimulus strength based on the determined waveform, $T_{STIM}$ denotes a stimulus duration based on the determined waveform, $R_E$ denotes a resistance of the target, $C_E$ denotes a capacitance of the target, and $V_{OV}$ denotes a margin voltage.

The method may include applying the stimulus signal and the first stimulus signal to the target through an electrode.

In another general aspect, there is provided a stimulator including a controller configured to determine a waveform of a stimulus signal for a target, based on biological feedback of the target responding to a first stimulus signal, to calculate a bioimpedance of the target based on a voltage waveform measured by applying the stimulus signal with the determined waveform to the target, and to determine an operating voltage of the stimulator based on the determined waveform and the calculated bioimpedance.

The controller may be configured to determine the waveform by adjusting a stimulus strength and a stimulus duration of the first stimulus signal.

The controller may be configured to determine an optimum stimulus strength to minimize a power consumption of the stimulator, based on a first biological feedback to a stimulus signal of a maximum stimulus duration and a gradually increasing stimulus strength, determine an optimum stimulus duration to minimize the power consumption of the stimulator, based on a second biological feedback to a stimulus signal of the optimum stimulus strength and a gradually increasing stimulus duration, and determine the waveform based on the optimum stimulus strength and the optimum stimulus duration.

The controller may be configured to detect a voltage of a first point and a voltage of a second point from the voltage waveform, and determine the bioimpedance based on the voltage of the first point and the voltage of the second point.

The bioimpedance may include a resistance and a capacitance of the target, and wherein the controller may be configured to calculate the resistance based on a first voltage measured, in response to charges being injected by the stimulus signal with the determined waveform, and calculate the capacitance based on a second voltage measured, in response to charges being extracted by the stimulus signal with the determined waveform.

The stimulator may include a feedback detector configured to detect the biological feedback at a measurement point of the target.

The stimulator may include a digital-to-analog converter (DAC) configured to apply any one or any combination of the first stimulus signal and the stimulus signal with the determined waveform to the target, and a power supply configured to supply the operating voltage to the DAC.

The stimulator may include a voltage measurer configured to measure a voltage generated, in response to the stimulus signal with the determined waveform being applied to the target.

The target may generate a spike signal in response to the first stimulus signal, and the feedback detector may be configured to detect the spike signal.

In another general aspect, there is provided a stimulator may include a feedback detector configured to detect biological feedback of a target responding to a detection stimulus signal, a controller configured to determine a waveform of an optimum stimulus signal based on the detected biological feedback, a voltage measurer configured to measure a voltage generated in response to the optimum stimulus signal being applied to the target, and a power supply configured to provide an operating voltage of the stimulator based on the measured voltage.

The controller may be configured to determine the waveform of the optimum stimulus signal by adjusting a stimulus strength and a stimulus duration of the detection stimulus signal.

The controller may be configured to calculate a bioimpedance of the target based on a waveform of the measured voltage, and determine the operating voltage based on the bioimpedance and the waveform of the optimum stimulus signal.

The controller may be configured to determine an optimum stimulus strength to minimize a power consumption of the stimulator, based on a first biological feedback to a stimulus signal of a maximum stimulus duration and a gradually increasing stimulus strength, determine an optimum stimulus duration to minimize the power consumption of the stimulator, based on a second biological feedback to a stimulus signal of the optimum stimulus strength and a gradually increasing stimulus duration, and determine the waveform of the optimum stimulus signal based on the optimum stimulus strength and the optimum stimulus duration.

The controller may be configured to detect a voltage of a first point and a voltage of a second point from a waveform of the measured voltage, and determine a bioimpedance of the target based on the voltage of the first point and the voltage of the second point.

The stimulator may include a digital-to-analog converter (DAC) controlled by the controller to apply any one or any combination of a stimulus signal for a charge insertion to the target, a stimulus signal for a charge extraction to the target, and the optimum stimulus signal to the target.

Other features and aspects will be apparent from the following detailed description, the drawings, and the claims.

Figure 1:
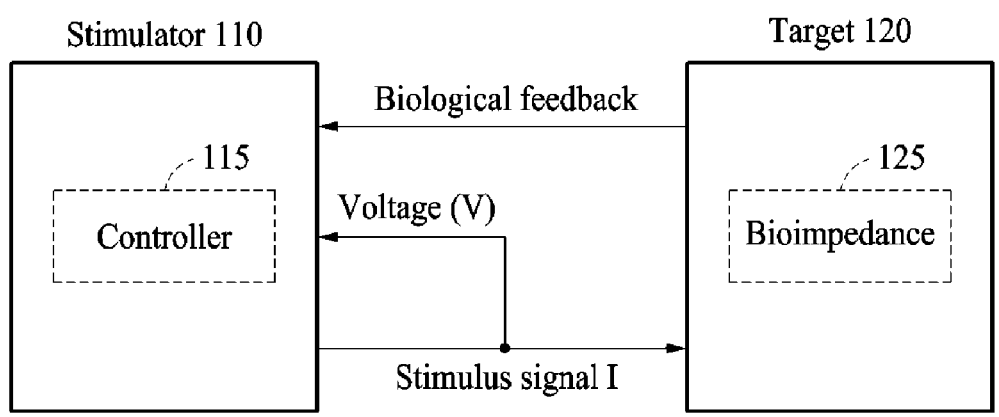
FIG. 1 illustrates an example of a stimulator and a target to be stimulated.

Throughout the drawings and the detailed description, unless otherwise described or provided, the same drawing reference numerals will be understood to refer to the same elements, features, and structures. The drawings may not be to scale, and the relative size, proportions, and depiction of elements in the drawings may be exaggerated for clarity, illustration, and convenience.

DETAILED DESCRIPTION

The following detailed description is provided to assist the reader in gaining a comprehensive understanding of the methods, apparatuses, and/or systems described herein. However, various changes, modifications, and equivalents of the methods, apparatuses, and/or systems described herein will be apparent after gaining a thorough understanding of the disclosure of this application. For example, the sequences of operations described herein are merely examples, and are not limited to those set forth herein, but may be changed as will be apparent after an understanding of the disclosure of this application, with the exception of operations necessarily occurring in a certain order. Also, descriptions of features that are known in the art may be omitted for increased clarity and conciseness.

The features described herein may be embodied in different forms, and are not to be construed as being limited to the examples described herein. Rather, the examples described herein have been provided merely to illustrate some of the many possible ways of implementing the methods, apparatuses, and/or systems described herein that will be apparent after an understanding of the disclosure of this application.

The following structure or functions are exemplary to merely describe a technical concept, and the scope of the examples is not limited to the descriptions provided in the present specification. Various changes and modifications may be made to the examples, and the examples are not construed as limited to the disclosure.

Although terms of "first" or "second" are used to explain various components, the components are not limited to the terms. These terms should be used only to distinguish one component from another component. For example, a "first" component may be referred to as a "second" component, or similarly, and the "second" component may be referred to as the "first" component within the scope of the right according to the concept of the present disclosure.

As used herein, the singular forms are intended to include the plural forms as well, unless the context clearly indicates otherwise.

FIG. 1 illustrates an example of a stimulator 110 and a target 120 to be stimulated. Referring to FIG. 1, the stimulator 110 applies a stimulus signal I to the target 120.

The stimulus signal I is expressed by, for example, a waveform of a current. The target 120 includes, for example, various body parts such as a brain, a heart, or a muscle. In another example, the target 120 corresponds to a cell, a tissue or an organ. For example, the target 120 is one of a brain cell, a brain tissue or the brain itself. Applying of the stimulus signal I to the target 120 includes applying the stimulus signal I to portions around the target 120 to apply the stimulus signal I to the target 120. For example, the stimulator 110 applies the stimulus signal I to portions around a heart to apply the stimulus signal I to the heart.

The stimulator 110 stimulates the target 120 for treatment, rehabilitation and cosmetic purposes. For example, the stimulator 110 is used as a medical device, for example, a deep brain stimulator, a pacemaker, an electrical muscle stimulator, a physical therapy device or an electric needle. The electrical muscle stimulator and the electric needle are used for health purposes, such as, for example, relaxation of muscles, medical purposes, growth of muscles, correction of shapes of muscles. In an example, a medical device incorporating the stimulator 110 is attached to a body or inserted into the body and applies an electrical stimulation to the body. In another example, the stimulator 110 is used for cosmetic purposes, such as, for example, a skin care or scar repair, growth of muscles, correction of shapes of muscles, or lipolysis.

The stimulator 110 applies the stimulus signal I to the target 120 based on an operating voltage of the stimulator 110. A power loss occurs when the stimulator 110 operates at an operating voltage higher than a desired voltage. For example, a characteristic, for example, an impedance, of the target 120, is determined based on a type of the target 120.

When the operating voltage of the stimulator 110 is determined regardless of the characteristic of the target 120, a power efficiency decreases. For example, in comparison to a first body part, a second body part responds to a weak stimulus signal, based on characteristics of body parts, when the same operating voltage is applied to both body parts, the stimulator 110 may consume a power higher than desired power. In this example, when a stimulus signal is applied to the second body part, the operating voltage may be decreased in comparison to when a stimulus signal is applied to the first body part. Accordingly, the stimulator 110 may operate with a higher efficiency. In an example, the stimulator 110 searches for an optimum operating voltage depending on circumstances, and operates with a high efficiency at the optimum operating voltage.

The stimulator 110 includes a controller 115. The controller 115 includes a hardware module and/or a processor as described below. The stimulator 110 may further include a memory located inside or outside the controller 115. The memory may store instructions executed by the controller 115 and data used to control the stimulator 110. In an example, the controller 115 executes the instructions stored in the memory and performs operations described below.

In an example, the stimulus signal I includes a detection stimulus signal $I_1$ and an optimum stimulus signal $I_2$. The detection stimulus signal $I_1$ is, for example, a signal applied to the target 120 to detect an optimum stimulus strength and an optimum stimulus duration. The optimum stimulus signal $I_2$ is a signal applied to the target 120, for example, of the optimum stimulus strength and for the optimum stimulus duration. The optimum stimulus strength and the optimum stimulus duration of the optimum stimulus signal $I_2$ is based on the detection stimulus signal $I_1$. The stimulator 110 operates based on the optimum stimulus signal $I_2$, and thus the power efficiency is increased.

The stimulator 110 determines a waveform of the optimum stimulus signal $I_2$ while applying the detection stimulus signal $I_1$ to the target 120. In an example, the waveform of the optimum stimulus signal $I_2$ is determined by a stimulus strength and a stimulus duration. The stimulus strength indicates an amplitude of a stimulus signal, and the stimulus duration indicates a duration of a stimulus signal. The stimulator 110 detects biological feedback of the target 120 while adjusting a stimulus strength and a stimulus duration of the detection stimulus signal $I_1$. The stimulator 110 determines the waveform of the optimum stimulus signal $I_2$ based on the detected biological feedback. An optimum stimulus strength and an optimum stimulus duration to minimize a power consumption of the stimulator 110 is determined based on the detected biological feedback.

Biological feedback is detected by a feedback detector that may be located inside or outside the stimulator 110. For example, the target 120 responds to a stimulus signal and generates a spike signal, and the feedback detector detects biological feedback based on the generated spike signal. The controller 115 determines whether biological feedback is generated, based on an output signal of the feedback detector.

The controller 115 detects the optimum stimulus strength and the optimum stimulus duration by changing the stimulus strength and the stimulus duration of the detection stimulus signal $I_1$ based on a pattern. In an example, the controller 115 changes the detection stimulus signal $I_1$ to have a maximum stimulus duration and a gradually increasing stimulus strength, and determines an optimum stimulus strength based on initial biological feedback responding to the detection stimulus signal $I_1$. In another example, the controller 115 changes the detection stimulus signal $I_1$ to have the optimum stimulus strength and a gradually increasing stimulus duration, and determines an optimum stimulus duration based on initial biological feedback responding to the detection stimulus signal $I_1$.

When the waveform of the optimum stimulus signal $I_2$ is determined, the controller 115 controls the operating voltage of the stimulator 110 based on the determined waveform. The controller 115 controls the operating voltage of the stimulator 110 to minimize a power loss. An example of controlling the operating voltage is further described below.

In an example, the controller 115 determines a minimum operating voltage for the stimulator 110 while applying the optimum stimulus signal $I_2$ with the determined waveform to the target 120. The minimum operating voltage is a lowest operating voltage to generate biological feedback when the optimum stimulus signal $I_2$ is applied to the target 120.

For example, the controller 115 controls the operating voltage of the stimulator 110 to gradually decrease while applying the optimum stimulus signal $I_2$ to the target 120, and determines whether biological feedback is detected. When the biological feedback is not detected as the operating voltage decreases, the controller 115 sets an operating voltage in which the biological feedback is not detected as a reference voltage. The controller 115 sets the minimum operating voltage to be higher than the reference voltage. For example, the controller 115 sets the minimum operating voltage to be higher than the reference voltage by a margin voltage. In response to the stimulator 110 operating at the minimum operating voltage, the power loss may be minimized, and thus the power efficiency may increase.

In another example, the controller 115 calculates a compliance voltage of the stimulator 110 and determines the operating voltage to be higher than the compliance voltage. The compliance voltage is a voltage used to operate the stimulator 110 normally. The controller 115 enhances a power efficiency of the stimulator 110 by maintaining the operating voltage to be within a range near the compliance voltage. The compliance voltage of the stimulator 110 is determined by a bioimpedance 125 and the waveform of the optimum stimulus signal $I_2$. Because both the bioimpedance 125 and the waveform of the optimum stimulus signal $I_2$ are used to determine the compliance voltage, the compliance voltage is accurately calculated in comparison to the minimum operating voltage.

The bioimpedance 125 is obtained by modeling a load characteristic of the target 120 and includes a resistance and a capacitance of the target 120. The controller 115 calculates the bioimpedance 125 based on a waveform of a voltage V measured by applying the optimum stimulus signal $I_2$ to the target 120. For example, the controller 115 detects voltages of two different points in the waveform of the voltage V and calculates the resistance and the capacitance of the target 120 based on the detected voltages.

The controller 115 determines the waveform of the optimum stimulus signal $I_2$ and the bioimpedance 125, determines the compliance voltage of the stimulator 110 based on the determined waveform and the determined bioimpedance 125, and determines the operating voltage of the stimulator 110 based on the compliance voltage. The controller 115 controls the stimulator 110 to apply the optimum stimulus signal $I_2$ to the target 120 at the determined operating voltage. Thus, a power loss of the stimulator 110 may be minimized.

Figure 2:
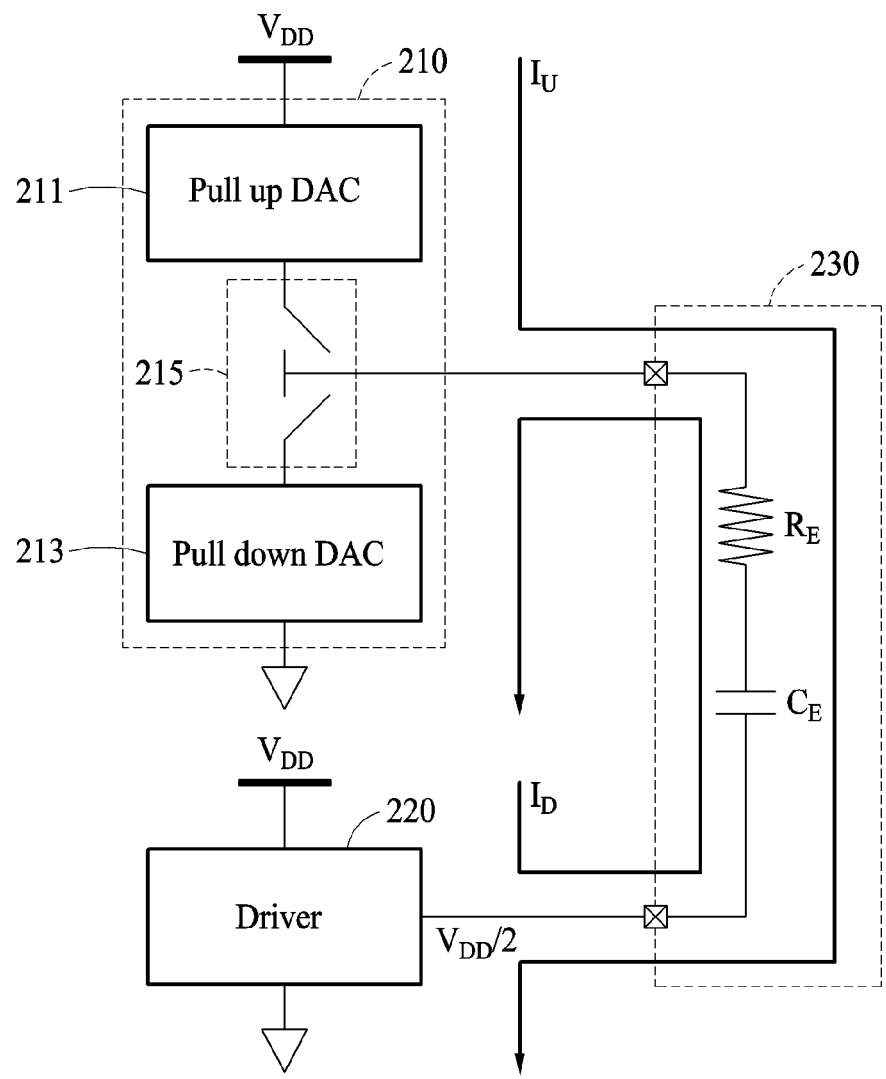
FIG. 2 illustrates an example of a digital-to-analog converter (DAC) and a driver.

FIG. 2 illustrates an example of a digital-to-analog converter (DAC) 210 and a driver 220. Referring to FIG. 2, the DAC 210 includes a pull up DAC 211, a pull down DAC 213 and a switching circuit 215. Based on a control signal transmitted by a controller of a stimulator, the switching circuit 215 alternately connects the pull up DAC 211 and the pull down DAC 213 to a target 230 to be stimulated. When the pull up DAC 211 is connected to the target 230, a stimulus signal $I_U$ for a charge injection is applied to the target 230. When the pull down DAC 213 is connected to the target 230, a stimulus signal $I_D$ for a charge extraction is applied to the target 230. The stimulus signals $I_U$ and $I_D$ flow in opposite directions, and correspond to the stimulus signal I of FIG. 1. The driver 220 receives a supplied operating voltage $V_{DD}$, and supplies a voltage $V_{DD}/2$ that is a half of the operating voltage $V_{DD}$ to the target 230. The stimulus signals $I_U$ and $I_D$ are supplied to the target 230 that includes a resistor $R_E$ and a capacitor $C_E$ based on the voltage $V_DD/2$ supplied by the driver 220.

Figure 3:
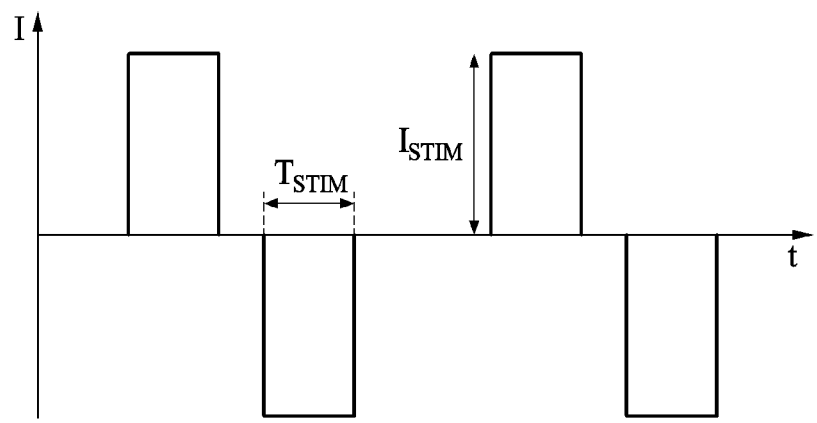
FIG. 3 illustrates an example of a waveform of a stimulus signal.

FIG. 3 illustrates an example of a waveform of a stimulus signal. The stimulus signal has a square wave as shown in FIG. 3. The example shown in FIG. 3 is only a non-exhaustive illustrations of the waveform of the stimulus signal, and other shapes of the waveform of the stimulus signal, for example, a sine wave or a triangle wave, are considered to be well within the scope of the present disclosure. A stimulus strength $I_{STIM}$ indicates an amplitude of the stimulus signal, and a stimulus duration $T_{STIM}$ indicates a duration of the stimulus signal. The stimulus signal includes a positive pulse and a negative pulse that are formed by the pull up DAC 211 and the pull down DAC 213 of FIG. 2. An interval between the positive pulse and the negative pulse is set in advance and is adjusted. A controller of a stimulator determines an optimum stimulus strength and an optimum stimulus duration based on biological feedback detected by adjusting a stimulus strength $I_{STIM}$ and a stimulus duration $T_{STIM}$ of a stimulus signal, and determines a waveform of a stimulus signal for a target to be stimulated, based on the optimum stimulus strength and the optimum stimulus duration. In an example, the stimulus signal and the stimulus signal for the target correspond to the detection stimulus signal $I_1$ and the optimum stimulus signal $I_2$ described above with reference to FIG. 1, respectively.

Figure 4:
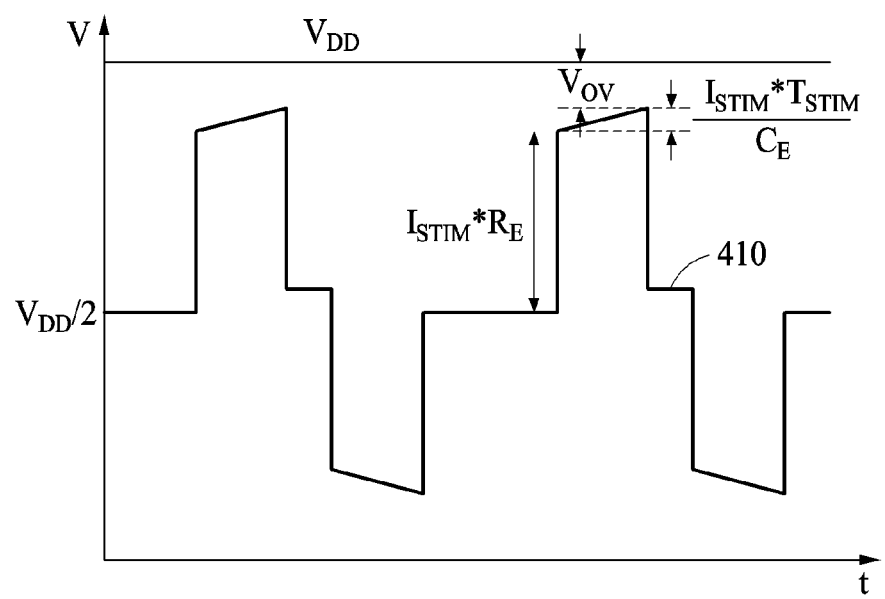
FIG. 4 illustrates an example of a voltage waveform based on a stimulus signal.

FIG. 4 illustrates an example of a voltage waveform 410 based on a stimulus signal. A controller of a stimulator acquires the voltage waveform 410 by applying, to a target to be stimulated, a stimulus signal that is based on a stimulus strength $I_{STIM}$ and a stimulus duration $T_{STIM}$. Referring to FIG. 4, when a value of $V_{DD}/2$ is determined to be greater than a sum obtained by adding up a value of "$I_{STIM} \times R_E$," a value of "$I_{STIM} \times T_{STIM}/C_E$," and a value of $V_{OV}$, the stimulator may operate normally. In this example, $R_E$ denotes a resistance of the target, $C_E$ denotes a capacitance of the target, and $V_{OV}$ denotes a margin voltage. Thus, a compliance voltage $V_C$ of the stimulator is represented by Equation 1 shown below.

$$V_C = 2 \times (I_{STIM} \times R_E + I_{STIM} \times T_{STIM}/C_E + V_{OV}) \qquad \text{[Equation 1]}$$

The controller determines an operating voltage $V_{DD}$ of the stimulator to be higher than, but substantially close to the compliance voltage $V_C$.

Figure 5:
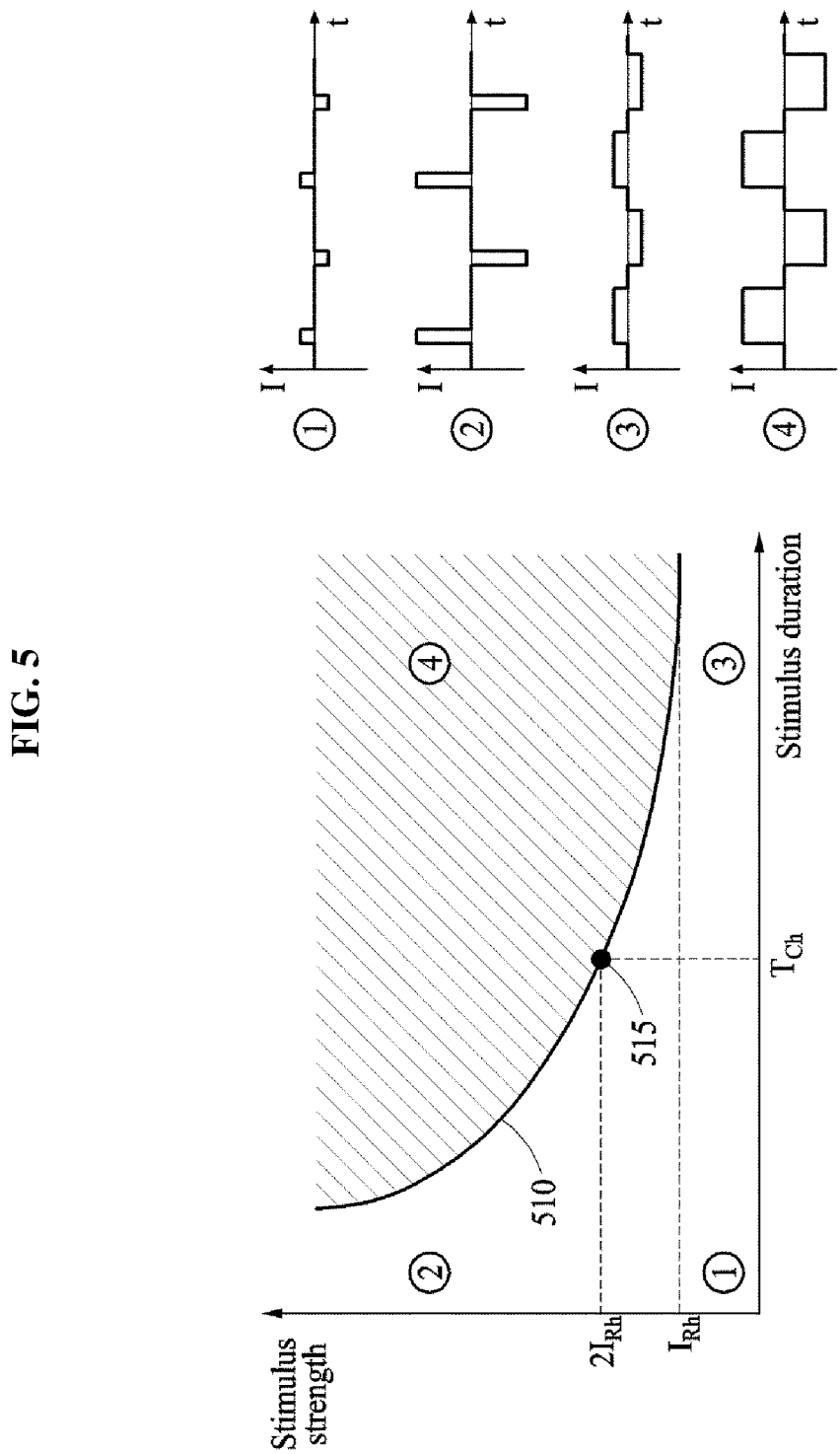
FIG. 5 illustrates an example of a feedback portion based on a stimulus duration and a stimulus strength.

FIG. 5 illustrates an example of a feedback portion based on a stimulus duration and a stimulus strength. Referring to FIG. 5, curve 510 represents neural response properties, when a neuron is stimulated by a stimulus strength less than a threshold strength for an indefinite duration, or stimulated by an indefinite stimulus strength for a duration less than a threshold duration, the neuron does not respond.

Referring to FIG. 5, region ① indicates an example in which a stimulus signal with a stimulus strength less than the threshold strength and a stimulus duration less than the threshold duration is applied to a neuron. Region ② indicates an example in which a stimulus signal with a stimulus strength greater than or equal to the threshold strength and a stimulus duration less than the threshold duration is applied to the neuron. Region ③ indicates an example in which a stimulus signal with a stimulus strength less than the threshold strength and a stimulus duration greater than or equal to the threshold duration is applied to the neuron. Region ④ indicates an example in which a stimulus signal with a stimulus strength greater than or equal to the threshold strength and a stimulus duration greater than or equal to the threshold duration is applied to the neuron. The neuron responds to the stimulus signal of region ④. In a graph of FIG. 5, an upper right portion corresponding to example ④ indicates that the neuron responds to the stimulus signal, and the other portion indicates that the neuron does not respond.

When a stimulus strength corresponding to an indefinite stimulus duration is defined as $I_{Rh}$ and a stimulus duration for which the neuron responds at a stimulus strength of $2I_{Rh}$ is defined as $T_{Ch}$ based on the curve 510, a relationship between a stimulus signal and a stimulus strength of the neuron is represented by Equation 2 shown below.

$$I(t) = I_{Rh}(1 + t/T_{Ch}) \quad \text{[Equation 2]}$$

$I_{Rh}$ denotes a rheobase current and $T_{Ch}$ denotes a chronaxie time. Based on Equation 2, an amount $Q_{STIM}$ of charge of the stimulus signal is represented by Equation 3 shown below.

$$Q_{STIM}(t) = I_{Rh}(1 + t/T_{Ch})t \quad \text{[Equation 3]}$$

Based on Equation 3, energy used for stimulation of a neuron is represented by "$I_{STIM} \times Q_{STIM}(t)$," and has a minimum value at $2T_{Ch}$ and rheobase current $I_{Rh}$. Thus, at a point 515 at which the energy is minimized, an optimum stimulus strength and an optimum stimulus duration are determined. An example of a process of determining an optimum stimulus strength and an optimum stimulus duration is described with reference to FIG. 6.

Figure 6:
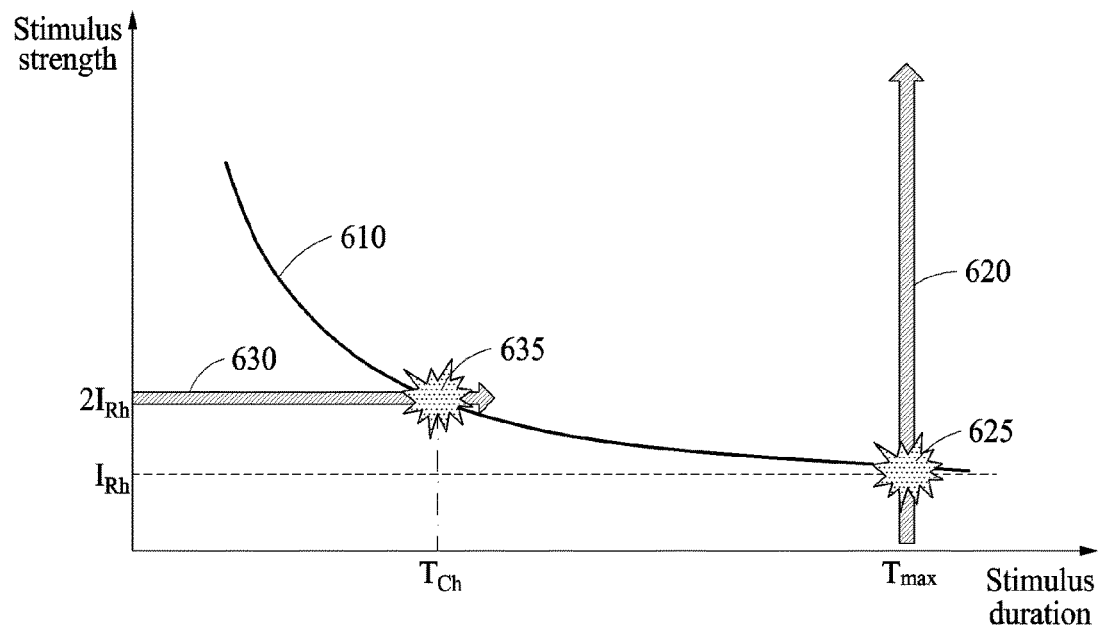
FIG. 6 illustrates an example of a process of determining an optimum stimulus strength and an optimum stimulus duration.

FIG. 6 illustrates an example of a process of determining an optimum stimulus strength and an optimum stimulus duration. In FIG. 6, a curve 610 represents neural response properties.

A controller of a stimulator determines an optimum stimulus strength based on biological feedback corresponding to a stimulus signal that is based on a maximum stimulus duration $T_{max}$ and a gradually increasing stimulus strength. For example, the controller senses initial biological feedback responding to the stimulus signal that is based on the maximum stimulus duration $T_{max}$ and the gradually increasing stimulus strength, and determines a stimulus strength corresponding to the sensed initial biological feedback as a rheobase current $I_{Rh}$. In this example, the stimulus strength gradually increases in a direction indicated by an arrow 620, and the initial biological feedback is sensed at a point 625. The controller determines the optimum stimulus strength to be twice the rheobase current $I_{Rh}$. In an example, the maximum stimulus duration $T_{max}$ is set in advance based on a type of a target to be stimulated and a unit of the target, and is set to, for example, a duration of 100 microseconds (μs) to 2 milliseconds (ms).

In an example, the controller determines an optimum stimulus duration based on biological feedback corresponding to a stimulus signal that is based on an optimum stimulus strength and a gradually increasing stimulus duration. For example, the controller senses initial biological feedback responding to the stimulus signal that is based on the optimum stimulus strength corresponding to $2I_{Rh}$ and the gradually increasing stimulus duration, and determines a stimulus duration corresponding to the sensed initial biological feedback as a chronaxie time $T_{Ch}$. In an example, the stimulus duration gradually increases in a direction indicated by an arrow 630, and the initial biological feedback is sensed at a point 635. The controller determines the optimum stimulus duration as the chronaxie time $T_{Ch}$. In an example, the controller determines a waveform of an optimum stimulus signal for the target based on the determined optimum stimulus strength and the determined optimum stimulus duration. When the optimum stimulus signal is applied to the target, a power efficiency may be enhanced in comparison to when another stimulus signal is applied to the target.

Figure 7:
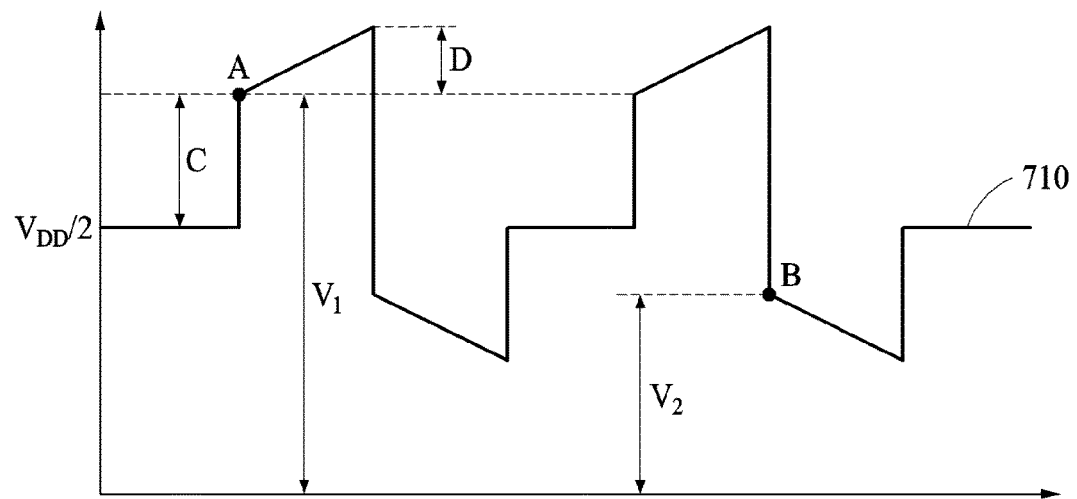
FIG. 7 illustrates an example of a process of calculating a bioimpedance.

FIG. 7 illustrates an example of a process of calculating a bioimpedance. FIG. 7 illustrates a voltage waveform 710 measured by applying a stimulus signal based on a stimulus strength $I_{STIM}$ and a stimulus duration $T_{STIM}$ to a target to be stimulated.

In an example, a controller of a stimulator detects a voltage of a first point and a voltage of a second point in the voltage waveform 710, and calculates a resistance and a capacitance of the target based on the detected voltages. For example, the controller detects a voltage $V_1$ of a point A and a voltage $V_2$ of a point B in the voltage waveform 710, and calculates the resistance and the capacitance of the target based on the voltages $V_1$ and $V_2$. The controller calculates the resistance based on the voltage $V_1$ measured at the point A after charges are injected by a stimulus signal. In FIG. 7, the voltage $V_1$ has a sum of $V_{DD}/2$ and C, and C has a value obtained by multiplying $I_{STIM}$ by $R_E$. The voltage $V_1$ is represented by Equation 4 shown below.

$$V_1 = V_{DD}/2 + I_{STIM} \times R_E \quad \text{[Equation 4]}$$

A resistance $R_E$ in Equation 4 is represented by Equation 5 shown below.

$$R_E = \frac{V_1 - V_{DD}/2}{I_{STIM}} \quad \text{[Equation 5]}$$

In an example, the controller calculates the capacitance based on the voltage $V_2$ measured at the point B after charges are extracted by a stimulus signal. In FIG. 7, the voltage $V_2$ has a value obtained by subtracting 2C from a sum of the voltage $V_1$ and D, and D has a value obtained by "$I_{STIM} \times T_{STIM}/C_E$." Accordingly, the voltage $V_2$ is represented by Equation 6 shown below and Equation 7 is obtained based on Equations 5 and 6.

$$V_2 = V_1 + D - 2 \times (I_{STIM} \times R_E) \quad \text{[Equation 6]}$$

$$V_2 = V_{DD}/2 + I_{STIM} \times T_{STIM}/C_E - I_{STIM} \times R_E \quad \text{[Equation 7]}$$

A capacitance $C_E$ in Equation 7 is represented by Equation 8 shown below.

$$C_E = \frac{I_{STIM} \times T_{STIM}}{V_2 - V_{DD}/2 + I_{STIM} \times R_E} \quad \text{[Equation 8]}$$

The controller uses an optimum stimulus strength and an optimum stimulus duration as a stimulus strength $I_{STIM}$ and a stimulus duration $T_{STIM}$, to obtain the resistance $R_E$ and the capacitance $C_E$. Accordingly, the controller acquires a bioimpedance from the voltage waveform 710.

In FIG. 7, the stimulus signal has a square wave, however, there is no limitation thereto. As described above, the stimulus signal of FIG. 7 is only a non-exhaustive illustrations of the waveform of the stimulus signal, and other shapes of the waveform of the stimulus signal, for example, a sine wave or a triangle wave, are considered to be well within the scope of the present disclosure. In an example of a sine wave or a triangle wave, the controller obtains a bioimpedance of the target similarly to the example of the square wave. In an example, when a stimulus signal has a sine wave, the controller applies the stimulus signal to the target, and measures a voltage waveform similar to the sine wave. The controller detects voltages at two points of the measured voltage waveform, and calculates a bioimpedance of the target based on the detected voltages. In another example, when a stimulus signal has a triangle wave, the controller applies the stimulus signal to the target and measures a voltage waveform similar to the triangle wave. The controller detects voltages at two points of the measured voltage waveform, and calculates a bioimpedance of the target based on the detected voltages. Similarly, the controller obtains a bioimpedance of the target for different waveforms.

The controller obtains a compliance voltage $V_C$ of the stimulator by substituting the stimulus strength $I_{STIM}$, the stimulus duration $T_{STIM}$, the resistance $R_E$, the capacitance $C_E$ and a margin voltage $V_{OV}$ into Equation 1. The controller substitutes an optimum stimulus strength determined to be twice a rheobase current as the stimulus strength $I_{STIM}$, and substitutes a chronaxie time as the stimulus duration $T_{STIM}$. When the compliance voltage $V_C$ is determined, the controller determines an operating voltage $V_{DD}$ of the stimulator to be higher than, but closest to the compliance voltage $V_C$.

Figure 8:
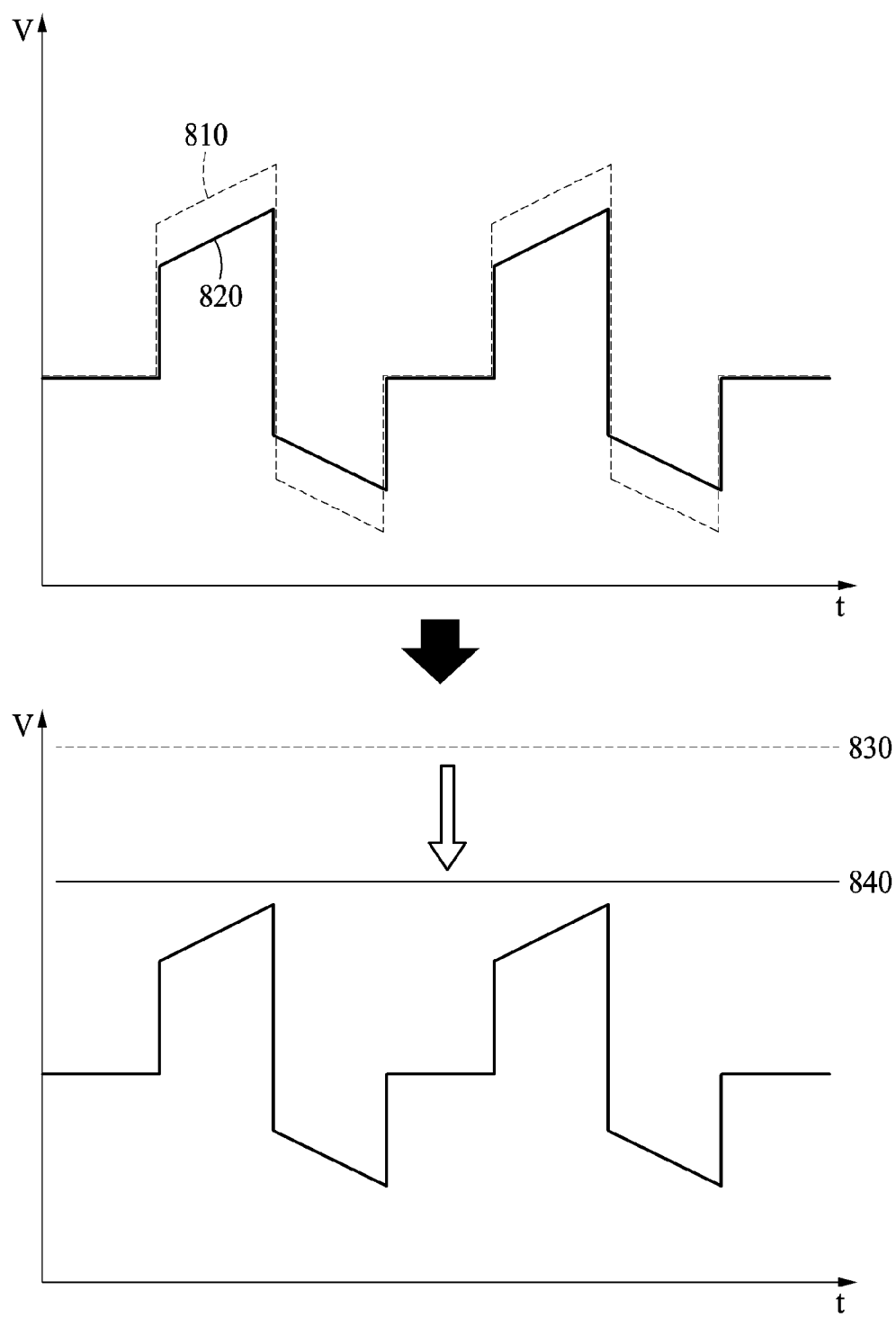
FIG. 8 illustrates an example of a change in a stimulus signal and an operating voltage.

FIG. 8 illustrates an example of a change in a stimulus signal and an operating voltage. FIG. 8 illustrates a voltage waveform 810, an optimum voltage waveform 820, and operating voltages 830 and 840.

The optimum voltage waveform 820 is obtained based on an optimum stimulus signal. Unlike the optimum voltage waveform 820, the voltage waveform 810 is measured when a stimulus signal with a stimulus strength greater than a stimulus strength of the optimum stimulus signal is applied to a target to be stimulated. As described above, because a neuron responds to a stimulus signal based on the optimum stimulus strength and the optimum stimulus duration, the target responds to both the voltage waveform 810 and the optimum voltage waveform 820. However, an amount of power to be consumed for the optimum voltage waveform 820 is less than that for the voltage waveform 810. Accordingly, it is possible to reduce an amount of power to be consumed in a stimulator based on the optimum stimulus strength and the optimum stimulus duration.

Also, a controller of the stimulator controls the operating voltages 830 and 840 based on a compliance voltage. Because both the operating voltages 830 and 840 are greater than the compliance voltage, the stimulator operates normally at both the operating voltages 830 and 840. Accordingly, the controller reduces an amount of power to be consumed in the stimulator using the operating voltage 840 that is less than the operating voltage 830. The controller applies the optimum stimulus strength and the optimum stimulus duration to the stimulus signal, and determines an operating voltage based on the compliance voltage, to minimize the amount of power to be consumed in the stimulator.

Figure 9:
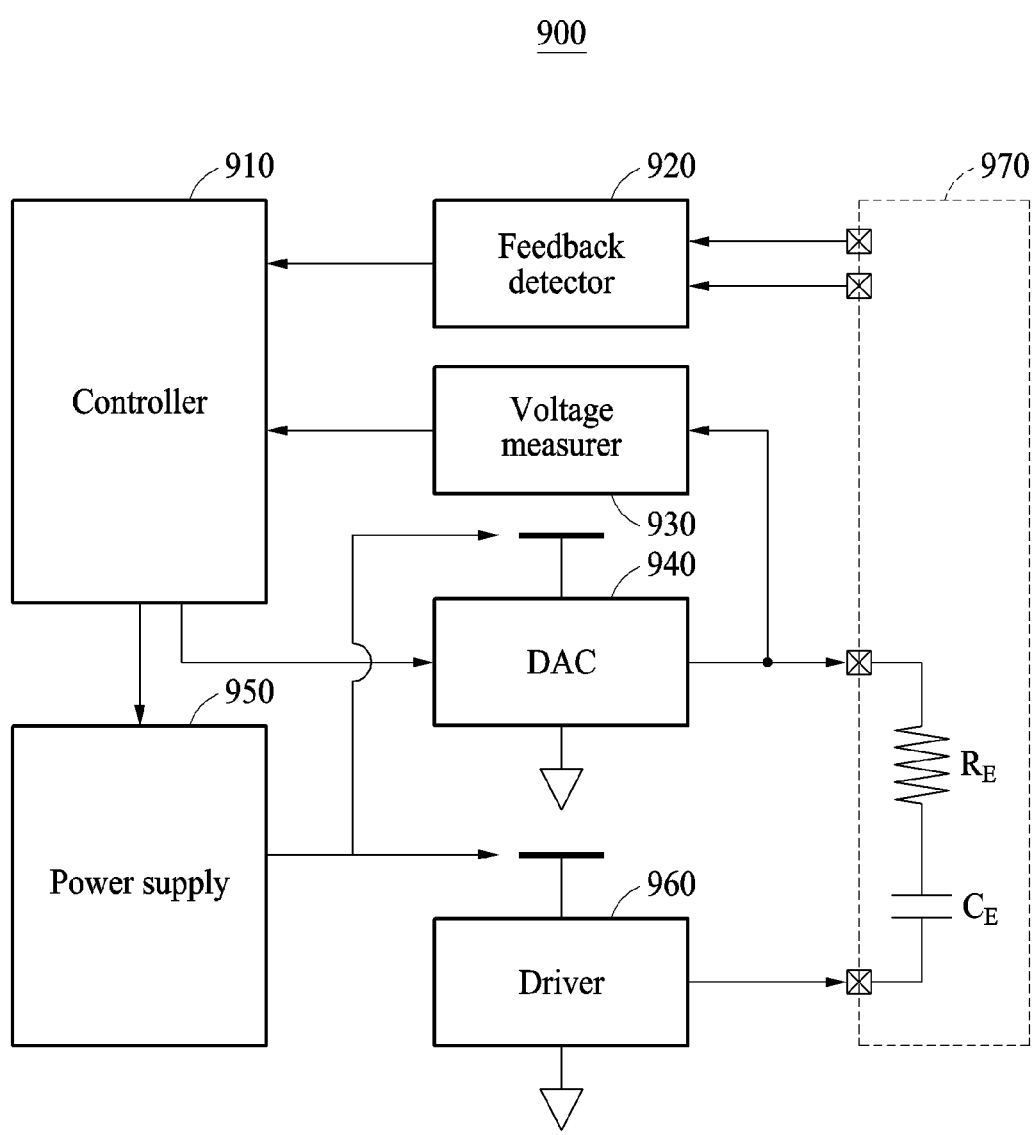
FIG. 9 illustrates an example of a stimulator.

FIG. 9 illustrates an example of a stimulator 900. Referring to FIG. 9, the stimulator 900 includes a controller 910, a feedback detector 920, a voltage measurer 930, a DAC 940, a power supply 950 and a driver 960.

For convenience of description, in the following description, an optimum stimulus strength and an optimum stimulus duration are denoted by $I_{STIM\_OPT}$ and $T_{STIM\_OPT}$, respectively. A stimulus strength other than the optimum stimulus strength and a stimulus duration other than the optimum stimulus duration are denoted by $I_{STIM}$ and $T_{STIM}$, respectively. Also, a detection stimulus signal with the stimulus strength $I_{STIM}$ and the stimulus duration $T_{STIM}$ is denoted by $I_1$, and an optimum stimulus signal with the optimum stimulus strength $I_{STIM\_OPT}$ and the optimum stimulus duration $T_{STIM\_OPT}$ is denoted by $I_2$. In addition, an optimum operating voltage is denoted by $V_{DD\_OPT}$, and an operating voltage other than the optimum operating voltage is denoted by $V_{DD}$.

The controller 910 transmits an output signal that is based on the stimulus strength $I_{STIM}$ and the stimulus duration $T_{STIM}$ to the DAC 940. In response to the output signal being received, the DAC 940 applies the detection stimulus signal $I_1$ to a target 970 to be stimulated. The DAC 940 applies the detection stimulus signal $I_1$ to the target 970 through an electrode that is in contact with the target 970. As described above, the DAC 940 includes a pull up DAC and a pull down DAC, and applies stimulus signals flowing in opposite directions to the target 970 through the pull up DAC and the pull down DAC. The power supply 950 supplies the operating voltage $V_{DD}$ to the DAC 940 and the driver 960. The driver 960 provides the target 970 with a voltage $V_{DD}/2$ that is a half of the operating voltage $V_{DD}$.

The feedback detector 920 detects biological feedback at a measurement point of the target 970 and transfers the detected biological feedback to the controller 910. In an example, the measurement point is away from a location at which a stimulus signal is applied. For example, the target 970 responds to a stimulus signal and generates a spike signal. The feedback detector 920 detects biological feedback based on the generated spike signal. The controller 910 determines whether biological feedback is generated, based on an output signal of the feedback detector 920. Although the feedback detector 920 is included in the stimulator as shown in FIG. 9, in other examples, the feedback detector 920 is separate from the stimulator or located outside the stimulator.

The controller 910 changes the detection stimulus signal $I_1$ applied to the target 970 by adjusting the stimulus strength $I_{STIM}$ and the stimulus duration $T_{STIM}$, and determines the optimum stimulus strength $I_{STIM\_OPT}$ and the optimum stimulus duration $T_{STIM\_OPT}$ based on the biological feedback detected by changing the detection stimulus signal $I_1$. As described above, the controller 910 determines the optimum stimulus strength $I_{STIM\_OPT}$ based on biological feedback corresponding to a stimulus signal that is based on a maximum stimulus duration $T_{max}$ and a gradually increasing stimulus strength, and determines the optimum stimulus duration $T_{STIM\_OPT}$ based on biological feedback corresponding to a stimulus signal that is based on the optimum stimulus strength $I_{STIM\_OPT}$ and a gradually increasing stimulus duration.

When the optimum stimulus strength $I_{STIM\_OPT}$ and the optimum stimulus duration $T_{STIM\_OPT}$ are determined, the controller 910 transmits an output signal that is based on the optimum stimulus strength $I_{STIM\_OPT}$ and the optimum stimulus duration $T_{STIM\_OPT}$ to the DAC 940. The DAC 940 applies the optimum stimulus signal $I_2$ to the target 970 based on the output signal. The voltage measurer 930 measures a voltage generated in response to the optimum stimulus signal $I_2$ being applied to the target 970, and transfers the measured voltage to the controller 910. The controller 910 calculates a bioimpedance of the target 970 including the resistance $R_E$ and the capacitance $C_E$ based on a waveform of the voltage measured by the voltage measurer 930. As described above, the controller 910 detects voltages at two points of the waveform of the voltage, and calculates the bioimpedance of the target 970 based on the detected voltages.

When the bioimpedance is calculated, the controller 910 determines a compliance voltage of the stimulator based on the optimum stimulus strength $I_{STIM\_OPT}$, the optimum stimulus duration $T_{STIM\_OPT}$ and the bioimpedance, and determines the optimum operating voltage $V_{DD\_OPT}$ based on the compliance voltage. The controller 910 transmits an output signal associated with the optimum operating voltage $V_{DD\_OPT}$ to the power supply 950. The power supply 950 supplies the optimum operating voltage $V_{DD\_OPT}$ to the DAC 940 and the driver 960 based on the output signal. Accordingly, the stimulator operates at the optimum operating voltage $V_{DD\_OPT}$.

Figure 10:
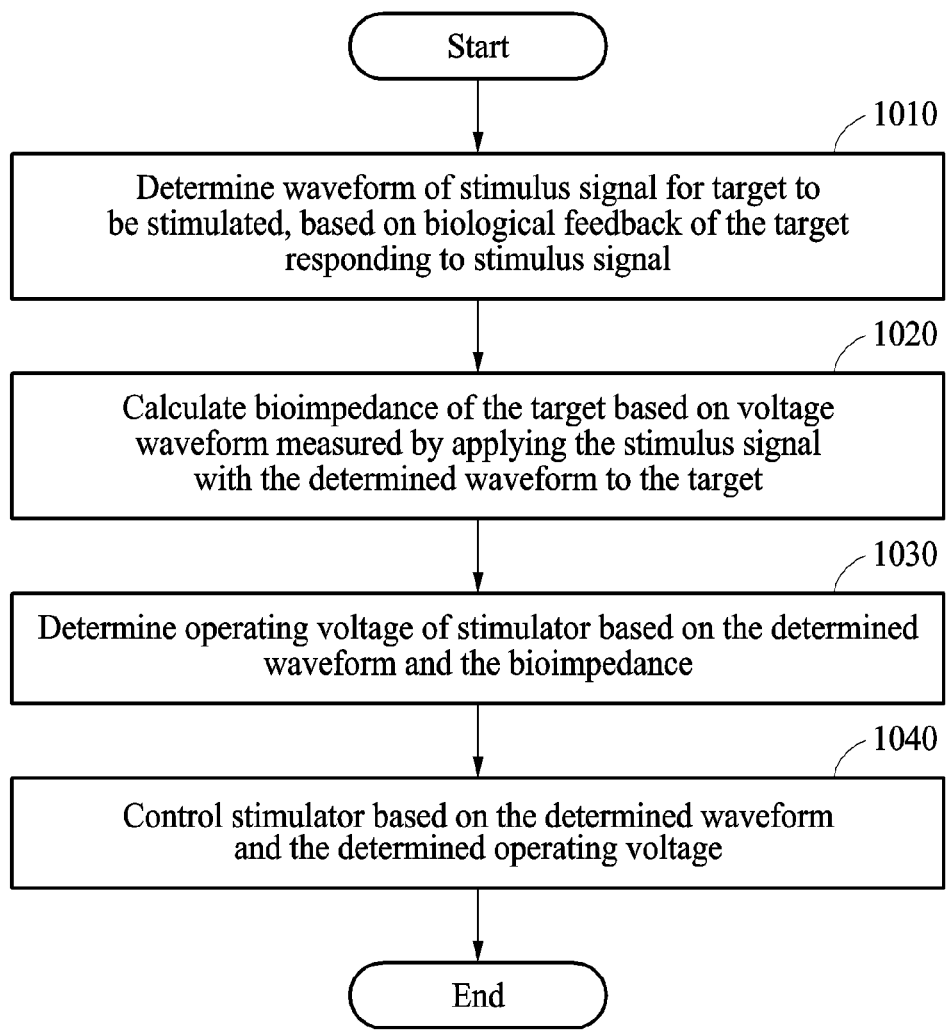
FIG. 10 is a diagram illustrating an example of a method of controlling a stimulator.

FIG. 10 illustrates an example of a method of controlling a stimulator. The operations in FIG. 10 may be performed in the sequence and manner as shown, although the order of some operations may be changed or some of the operations omitted without departing from the spirit and scope of the illustrative examples described. Many of the operations shown in FIG. 10 may be performed in parallel or concurrently. One or more blocks of FIG. 10, and combinations of the blocks, can be implemented by special purpose hardware-based computer that perform the specified functions, or combinations of special purpose hardware and computer instructions. In addition to the description of FIG. 10 below, the descriptions of FIGS. 1-9 is also applicable to FIG. 10, and are incorporated herein by reference. Thus, the above description may not be repeated here.

In operation 1010, a controller of the stimulator determines a waveform of a stimulus signal for a target to be stimulated, based on biological feedback of the target responding to a stimulus signal. In operation 1020, the controller calculates a bioimpedance of the target based on a voltage waveform measured by applying the stimulus signal with the determined waveform to the target. In operation 1030, the controller determines an operating voltage of the stimulator based on the determined waveform and the bioimpedance. In operation 1040, the controller controls the stimulator based on the determined waveform and the operating voltage.

The stimulator 110, controller 115, stimulator 900, controller 910, feedback detector 920, voltage measurer 930, and other apparatuses, units, modules, devices, and other components illustrated in FIGS. 1, 2 and 9 that perform the operations described herein with respect to FIG. 10 are implemented by hardware components. Examples of hardware components that may be used to perform the operations described in this application where appropriate include controllers, sensors, generators, drivers, memories, comparators, arithmetic logic units, adders, subtractors, multipliers, dividers, integrators, and any other electronic components configured to perform the operations described in this application. In other examples, one or more of the hardware components that perform the operations described in this application are implemented by computing hardware, for example, by one or more processors or computers. A processor or computer may be implemented by one or more processing elements, such as an array of logic gates, a controller and an arithmetic logic unit, a digital signal processor, a microcomputer, a programmable logic controller, a field-programmable gate array, a programmable logic array, a microprocessor, or any other device or combination of devices that is configured to respond to and execute instructions in a defined manner to achieve a desired result. In one example, a processor or computer includes, or is connected to, one or more memories storing instructions or software that are executed by the processor or computer. Hardware components implemented by a processor or computer may execute instructions or software, such as an operating system (OS) and one or more software applications that run on the OS, to perform the operations described in this application. The hardware components may also access, manipulate, process, create, and store data in response to execution of the instructions or software. For simplicity, the singular term "processor" or "computer" may be used in the description of the examples described in this application, but in other examples multiple processors or computers may be used, or a processor or computer may include multiple processing elements, or multiple types of processing elements, or both. For example, a single hardware component or two or more hardware components may be implemented by a single processor, or two or more processors, or a processor and a controller. One or more hardware components may be implemented by one or more processors, or a processor and a controller, and one or more other hardware components may be implemented by one or more other processors, or another processor and another controller. One or more processors, or a processor and a controller, may implement a single hardware component, or two or more hardware components. A hardware component may have any one or more of different processing configurations, examples of which include a single processor, independent processors, parallel processors, single-instruction single-data (SISD) multiprocessing, single-instruction multiple-data (SIMD) multiprocessing, multiple-instruction single-data (MISD) multiprocessing, and multiple-instruction multiple-data (MIMD) multiprocessing.

The methods illustrated in FIG. 10 that perform the operations described in this application are performed by computing hardware, for example, by one or more processors or computers, implemented as described above executing instructions or software to perform the operations described in this application that are performed by the methods. For example, a single operation or two or more operations may be performed by a single processor, or two or more processors, or a processor and a controller. One or more operations may be performed by one or more processors, or a processor and a controller, and one or more other operations may be performed by one or more other processors, or another processor and another controller. One or more processors, or a processor and a controller, may perform a single operation, or two or more operations.

Instructions or software to control a processor or computer to implement the hardware components and perform the methods as described above are written as computer programs, code segments, instructions or any combination thereof, for individually or collectively instructing or configuring the processor or computer to operate as a machine or special-purpose computer to perform the operations performed by the hardware components and the methods as described above. In one example, the instructions or software includes at least one of an applet, a dynamic link library (DLL), middleware, firmware, a device driver, an application program storing the method of preventing the collision. In one example, the instructions or software include machine code that is directly executed by the processor or computer, such as machine code produced by a compiler. In another example, the instructions or software include higher-level code that is executed by the processor or computer using an interpreter. Programmers of ordinary skill in the art can readily write the instructions or software based on the block diagrams and the flow charts illustrated in the drawings and the corresponding descriptions in the specification, which disclose algorithms for performing the operations performed by the hardware components and the methods as described above.

The instructions or software to control a processor or computer to implement the hardware components and perform the methods as described above, and any associated data, data files, and data structures, are recorded, stored, or fixed in or on one or more non-transitory computer-readable storage media. Examples of a non-transitory computer-readable storage medium include read-only memory (ROM), random-access programmable read only memory (PROM), electrically erasable programmable read-only memory (EEPROM), random-access memory (RAM), dynamic random access memory (DRAM), static random access memory (SRAM), flash memory, non-volatile memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, blue-ray or optical disk storage, hard disk drive (HDD), solid state drive (SSD), flash memory, a card type memory such as multimedia card micro or a card (for example, secure digital (SD) or extreme digital (XD)), magnetic tapes, floppy disks, magneto-optical data storage devices, optical data storage devices, hard disks, solid-state disks, and any other device that is configured to store the instructions or software and any associated data, data files, and data structures in a non-transitory manner and providing the instructions or software and any associated data, data files, and data structures to a processor or computer so that the processor or computer can execute the instructions.

While this disclosure includes specific examples, it will be apparent after gaining a thorough understanding of the disclosure of this application that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner, and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A method of controlling a stimulator, the method comprising:
   determining a waveform of a stimulus signal for a target based on a biological feedback of the target responding to a first stimulus signal;
   calculating a bioimpedance of the target based on a voltage waveform measured by applying the stimulus signal with the determined waveform to the target;
   determining an operating voltage of the stimulator based on the determined waveform and the calculated bioimpedance; and
   controlling the stimulator to stimulate the target based on the determined waveform and the determined operating voltage.

2. The method of claim 1, wherein the determining of the waveform comprises determining the waveform by adjusting a stimulus strength and a stimulus duration of the first stimulus signal.

3. The method of claim 1, wherein the determining of the waveform comprises:
   determining an optimum stimulus strength to minimize a power consumption of the stimulator based on a first biological feedback of the target responding to a stimulus signal of a maximum stimulus duration and a gradually increasing stimulus strength;
   determining an optimum stimulus duration to minimize the power consumption of the stimulator based on a second biological feedback of the target responding to a stimulus signal of the optimum stimulus strength and a gradually increasing stimulus duration; and
   determining the waveform based on the optimum stimulus strength and the optimum stimulus duration.

4. The method of claim 3, wherein the determining of the optimum stimulus strength comprises:
   sensing an initial biological feedback of the target responding to the stimulus signal that is based on the maximum stimulus duration and the gradually increasing stimulus strength;
   determining a stimulus strength corresponding to the sensed initial biological feedback to be a rheobase current; and
   determining the optimum stimulus strength to be twice the rheobase current.

5. The method of claim 3, wherein the determining of the optimum stimulus duration comprises:
   sensing an initial biological feedback of the target responding to the stimulus signal that is based on the optimum stimulus strength and the gradually increasing stimulus duration;
   determining a stimulus duration corresponding to the sensed initial biological feedback to be a chronaxie time; and
   determining the optimum stimulus duration to be the chronaxie time.

6. The method of claim 1, wherein the bioimpedance comprises a resistance and a capacitance of the target.

7. The method of claim 1, wherein the calculating of the bioimpedance comprises:
   detecting a voltage of a first point and a voltage of a second point from the voltage waveform; and
   calculating a resistance and a capacitance of the target based on the voltage of the first point and the voltage of the second point.

8. The method of claim 1, wherein the calculating of the bioimpedance comprises:
   calculating a resistance of the target based on a first voltage measured in response to charges being injected by the stimulus signal with the determined waveform; and
   calculating a capacitance of the target based on a second voltage measured in response to charges being extracted by the stimulus signal with the determined waveform.

9. The method of claim 8, wherein the resistance is calculated using the following equation:

$$R_E = \frac{V_1 - V_{DD}/2}{I_{STIM}}$$

wherein $R_E$ denotes the resistance, $V_1$ denotes the first voltage, $V_{DD}$ denotes an initial operating voltage of the stimulator, and $I_{STIM}$ denotes a stimulus strength based on the determined waveform.

10. The method of claim 8, wherein the capacitance is calculated using the following equation:

$$C_E = \frac{I_{STIM} \times T_{STIM}}{V_2 - V_{DD}/2 + I_{STIM} \times R_E}$$

wherein $C_E$ denotes the capacitance, $I_{STIM}$ denotes a stimulus strength based on the determined waveform, $T_{STIM}$ denotes a stimulus duration based on the determined waveform, $V_2$ denotes the second voltage, $V_{DD}$ denotes an initial operating voltage of the stimulator, and $R_E$ denotes the resistance.

11. The method of claim 1, wherein the determining of the operating voltage comprises:
calculating a compliance voltage of the stimulator based on the determined waveform and the bioimpedance; and
determining the operating voltage to be greater than the compliance voltage.

12. The method of claim 11, wherein the compliance voltage is calculated using the following equation:

$$V_C = 2 \times (I_{STIM} \times R_E + I_{STIM} \times T_{STIM}/C_E + V_{OV})$$

wherein $V_C$ denotes the compliance voltage, $I_{STIM}$ denotes a stimulus strength based on the determined waveform, $T_{STIM}$ denotes a stimulus duration based on the determined waveform, $R_E$ denotes a resistance of the target, $C_E$ denotes a capacitance of the target, and $V_{OV}$ denotes a margin voltage.

13. The method of claim 1, further comprising applying the stimulus signal and the first stimulus signal to the target through an electrode.

14. A non-transitory computer-readable medium storing instructions that, when executed by a processor, cause the processor to perform the method of claim 1.

15. A stimulator comprising:
a controller configured to:
determine a waveform of a stimulus signal for a target based on a biological feedback of the target responding to a first stimulus signal;
calculate a bioimpedance of the target based on a voltage waveform measured by applying the stimulus signal with the determined waveform to the target; and
determine an operating voltage of the stimulator based on the determined waveform and the calculated bioimpedance.

16. The stimulator of claim 15, wherein the controller is further configured to determine the waveform by adjusting a stimulus strength and a stimulus duration of the first stimulus signal.

17. The stimulator of claim 15, wherein the controller is further configured to:
determine an optimum stimulus strength to minimize a power consumption of the stimulator based on a first biological feedback of the target responding to a stimulus signal of a maximum stimulus duration and a gradually increasing stimulus strength;
determine an optimum stimulus duration to minimize the power consumption of the stimulator based on a second biological feedback of the target responding to a stimulus signal of the optimum stimulus strength and a gradually increasing stimulus duration; and
determine the waveform based on the optimum stimulus strength and the optimum stimulus duration.

18. The stimulator of claim 15, wherein the controller is further configured to:
detect a voltage of a first point and a voltage of a second point from the voltage waveform; and
determine the bioimpedance based on the voltage of the first point and the voltage of the second point.

19. The stimulator of claim 15, wherein the bioimpedance comprises a resistance and a capacitance of the target, and the controller is further configured to:
calculate the resistance based on a first voltage measured in response to charges being injected by the stimulus signal with the determined waveform; and
calculate the capacitance based on a second voltage measured in response to charges being extracted by the stimulus signal with the determined waveform.

20. The stimulator of claim 15, further comprising a feedback detector configured to detect the biological feedback at a measurement point of the target.

21. The stimulator of claim 20, wherein the target generates a spike signal in response to the first stimulus signal, and
the feedback detector is further configured to detect the spike signal.

22. The stimulator of claim 15, further comprising:
a digital-to-analog converter (DAC) configured to apply either one or both of the first stimulus signal and the stimulus signal with the determined waveform to the target; and
a power supply configured to supply the operating voltage to the DAC.

23. The stimulator of claim 15, further comprising a voltage measurer configured to measure a voltage generated in response to the stimulus signal with the determined waveform being applied to the target.

24. A stimulator comprising:
a feedback detector configured to detect a biological feedback of a target responding to a detection stimulus signal;
a controller configured to determine a waveform of an optimum stimulus signal based on the detected biological feedback;
a voltage measurer configured to measure a voltage generated in response to the optimum stimulus signal being applied to the target; and
a power supply configured to provide an operating voltage of the stimulator based on the measured voltage.

25. The stimulator of claim 24, wherein the controller is further configured to determine the waveform of the optimum stimulus signal by adjusting a stimulus strength and a stimulus duration of the detection stimulus signal.

26. The stimulator of claim 24, wherein the controller is further configured to:
calculate a bioimpedance of the target based on a waveform of the measured voltage; and
determine the operating voltage based on the bioimpedance and the waveform of the optimum stimulus signal.

27. The stimulator of claim 24, wherein the controller is further configured to:

determine an optimum stimulus strength to minimize a power consumption of the stimulator based on a first biological feedback of the target responding to a stimulus signal of a maximum stimulus duration and a gradually increasing stimulus strength;

determine an optimum stimulus duration to minimize the power consumption of the stimulator based on a second biological feedback of the target responding to a stimulus signal of the optimum stimulus strength and a gradually increasing stimulus duration; and determine the waveform of the optimum stimulus signal based on the optimum stimulus strength and the optimum stimulus duration.

28. The stimulator of claim 24, wherein the controller is further configured to:

detect a voltage of a first point and a voltage of a second point from a waveform of the measured voltage; and determine a bioimpedance of the target based on the voltage of the first point and the voltage of the second point.

29. The stimulator of claim 24, further comprising a digital-to-analog converter (DAC) controlled by the controller to apply to the target any one or any combination of any two or more of a stimulus signal for a charge insertion, a stimulus signal for a charge extraction, and the optimum stimulus signal.

* * * * *